United States Patent [19]

Boger et al.

[11] Patent Number: 5,550,059
[45] Date of Patent: Aug. 27, 1996

[54] FLUID SENSING PIPETTE

[75] Inventors: David L. Boger, Mishawaka;
Doraiswami Jaichandra, Granger;
Donald L. Jaworski, Mishawaka;
Joseph E. Perry, Osceola, all of Ind.

[73] Assignee: Bayer Corporation, Elkhart, Ind.

[21] Appl. No.: 358,111

[22] Filed: Dec. 16, 1994

Related U.S. Application Data

[63] Continuation-in-part of Ser. No. 200,675, Feb. 23, 1994, abandoned.

[51] Int. Cl.$^6$ ............................................. B01L 3/02
[52] U.S. Cl. ................... 436/54; 436/180; 422/100; 422/106; 73/304 C; 73/864.01
[58] Field of Search .................... 422/99, 100, 106; 436/54, 180; 73/304 R, 304 C, 864.01, 864.02, 864.11, 864.21, 864.24; 141/95, 130

[56]  References Cited

U.S. PATENT DOCUMENTS

| | | |
|---|---|---|
| 3,391,547 | 7/1968 | Kingston . |
| 3,635,094 | 1/1972 | Oberli . |
| 3,754,444 | 8/1973 | Ure et al. . |
| 4,276,258 | 6/1981 | Ginsberg et al. . |
| 4,276,260 | 6/1981 | Drbal et al. . |
| 4,326,851 | 4/1982 | Bello et al. . |
| 4,389,900 | 6/1983 | Gutierrez . |
| 4,487,836 | 12/1984 | Takayanagi et al. . |
| 4,577,514 | 3/1986 | Bradley et al. . |
| 4,736,638 | 4/1988 | Okawa et al. . |
| 4,818,492 | 4/1989 | Shimizu . |
| 4,897,244 | 1/1990 | Wallace et al. . |

FOREIGN PATENT DOCUMENTS

| | | |
|---|---|---|
| 035591 | 2/1990 | European Pat. Off. . |
| 1287148 | 8/1972 | United Kingdom . |

OTHER PUBLICATIONS

Olson, R., "Winding Problems Solved With Parylene Coating", Reprinted from Insulation/Circuits, 1978.
Humphrey, B., "The Application of Parylene Conformal Coating Technology To Archival And Artifact Conservation", Studies In Conservation, vol. 29, pp. 117–123, 1984.
"Parylene—A Gas Phase Polymer for Conservation of Historical Materials", Nova Tran Corp., Clear Lake, WI., pp. 1–8.
Olson, R. and Veaque, R., "Very Thin Conformal Coating For Contamination Control", Reprinted from Microcontamination, 1985.
"Parylene Conformal Coatings Specifications And Properties", Specialty Coating Systems, Inc., Indianapolis, IN, pp. 1–12, 1992.

(List continued on next page.)

*Primary Examiner*—Jeffrey R. Snay
*Attorney, Agent, or Firm*—Roger N. Coe

[57]  ABSTRACT

A fluid sensing pipette includes an outer conductive tube forming a first electrode and an inner conductive tube forming a second electrode. The inner conductive tube is disposed concentrically within the outer conductive tube. To insulate the inner conductive tube from the outer conductive tube, the inner conductive tube is coated with a thin, uniform, and consistent Parylene coating. A hydrophobic polymeric tube is disposed concentrically within the inner conductive tube to prevent cross-contamination between different biological samples aspirated into the pipette. The inner and outer conductive tubes are separately coupled to a level detection circuit which permits the pipette to detect entry of the pipette into a conductive fluid. The level detection circuit determines the impedance between the first and second electrodes and produces a control signal in response to the impedance falling below a predetermined threshold. A hydrophobic polymeric plug is disposed between the inner conductive tube and the polymeric tube in close proximity to a distal end of the polymeric tube so as to prevent fluid from entering between the inner conductive tube and the polymeric tube.

10 Claims, 3 Drawing Sheets

OTHER PUBLICATIONS

"The Source . . . For Complete Conformal Coating Materials, Systems and Services", Specialty Coating Systems, Inc., Indianapolis, IN, 1992.

"Abrasion Resistance Of Parylene And Other Conformal Circuit Board Coatings", Nova Tran Corp., Clear Lake, WI, pp. 1–7.

Weightman, H., "Microabrasive Blasting Solves Unusual Insulation Removal Problems", Reprinted from Insulation/Circuits, 1981.

The Parylene Press, Specialty Coating Systems, Inc., No. 14, Fall 1993.

"Current Protocols in Immunology" Unit 7.28, pp. 1–2 and 13–22, 1994 by John Wiley & Sons Inc.

5,550,059

FLUID SENSING PIPETTE

CROSS-REFERENCE TO RELATED APPLICATIONS

This application is a continuation-in-part of application Ser. No. 08/200,675, filed Feb. 23, 1994, now abandoned.

FIELD OF THE INVENTION

The present invention generally relates to a fluid sensing pipette for detecting fluid into which the pipette is immersed. More particularly, the present invention relates to a new and improved fluid level sensing pipette constructed to be self-cleaned quickly and to prevent cross-contamination between different biological samples.

BACKGROUND OF THE INVENTION

Automated analyzers commonly use pipettes to perform biological tests on a series of biological samples (e.g., urine specimens). An automated analyzer uses the pipette to cyclicly perform a sequence of steps. In each sampling cycle, the pipette first aspirates a biological sample from a sample tube and dispenses a portion of the sample onto a strip of multiple reagent pads. Next, if desired, the pipette dispenses the remaining portion of the sample into a specific gravity well in order to measure the specific gravity of the sample. Finally, the pipette is self-cleansed of residual sample by expelling cleaning solution, coupled to the proximal end of the pipette, from the distal tip thereof into a discharge basin. To clean the exterior of the pipette, the discharge basin may be constructed in the shape of a well sized to receive the pipette tip. The cleaning solution expelled from the pipette tip is forced by the well to surround the exterior of the tip, thereby cleaning it. At this point in time, the sampling cycle has been completed and the automated analyzer is ready to execute another cycle on another biological sample.

In order to detect when the pipette enters the sample in the sample tube, the pipette may be constructed with fluid sensing capabilities. One such fluid sensing pipette is described in U.S. Pat. No. 3,754,444 to Ure et al. This pipette includes an inner conductive tube forming a first electrode and an outer conductive tube forming a second electrode. The outer conductive tube is disposed concentric about the inner conductive tube and is insulated from the inner conductive tube by a plastic tubular sleeve. The inner and outer conductive tubes are coupled, by means of spaced wires, to level detection circuitry. When the inner and outer conductive tubes enter a sample within a sample tube, the level detection circuitry senses a change of the impedance between air and the sample and signals a motor to stop the descent of the pipette.

To maximize the efficiency at which biological tests are performed in an automated system, it is preferable to minimize the time period in each sampling cycle. To aid in this minimization of cycle time, the time period for cleansing the pipette tip should accordingly be minimized. A drawback of the foregoing fluid sensing pipette is that it is difficult to cleanse both the interior and exterior of the pipette in a relatively short period of time and with a minimal volume of cleaning solution. In particular, the outer conductive tube must be designed with a large enough diameter to accommodate the insulative plastic sleeve disposed between the inner and outer conductive tubes. The presence of the plastic sleeve significantly increases the required diametric size of the outer conductive tube which, in turn, increases the outer surface area of the outer conductive tube. Due to the increased outer surface area, a relatively large amount of cleaning solution would need to be expelled from the pipette tip in order to cleanse the exterior of the pipette tip. This would be a time-consuming operation.

Another drawback of the foregoing pipette is that the pipette may cause cross-contamination between different pipetted fluids because aqueous drops or constituents (e.g., proteins) of one pipetted fluid may carryover to the operation of the pipette on a different fluid. This cross-contamination may occur even though the pipette is cleansed with cleaning solution after it aspirates and dispenses each pipetted fluid. The reason for this is that aqueous drops of pipetted fluids strongly adhere to the inner surface of the inner conductive tube. Moreover, constituents such as proteins preferentially bind to the inner surface of the inner conductive tube.

Thus, a need exists for a fluid sensing pipette which overcomes the abovenoted drawbacks associated with the foregoing pipette.

SUMMARY OF THE INVENTION

An object of the present invention is to provide a fluid sensing pipette which minimizes the time period and volume of cleaning solution required to cleanse both the interior and exterior of the pipette tip.

Another object of the present invention is to provide a fluid sensing pipette which prevents cross-contamination between different biological samples.

Other objects and advantages of the invention will be apparent from the following detailed description and accompanying drawings.

In accordance with the present invention, the foregoing objects are realized by providing a fluid sensing pipette including an outer conductive tube forming a first electrode and an inner conductive tube forming a second electrode. The inner conductive tube is disposed concentrically within the outer conductive tube. To insulate the inner conductive tube from the outer conductive tube, the inner conductive tube is coated with a thin, uniform, and consistent Parylene coating. A hydrophobic polymeric tube is disposed concentrically within the inner conductive tube. The inner and outer conductive tubes are separately coupled to a level detection circuit which permits the pipette to detect entry of the pipette into a conductive fluid. The level detection circuit determines the impedance between the first and second electrodes and produces a control signal in response to the impedance falling below a predetermined threshold.

In a preferred embodiment, a hydrophobic polymeric plug is disposed between the inner conductive tube and the polymeric tube in close proximity to a distal end of the polymeric tube so as to prevent fluid from entering between the inner conductive tube and the polymeric tube. The plug prevents the polymeric tube from dilating and eventually pulling back into the inner conductive tube during a manufacturing process known as temperature cycling. In the temperature cycling process, the pipette is repeatedly heated and cooled to stabilize the length of a nozzle formed by the polymeric tube.

To use the fluid sensing pipette, cleaning solution is pumped into the polymeric tube via the proximal end thereof. Next, air is aspirated into the polymeric tube via the nozzle (distal end) thereof. After aspirating the air into the polymeric tube, a biological sample is aspirated into the polymeric tube via the nozzle thereof. The aspirated air creates an air gap between the cleaning solution and the aspirated biological sample. At least a portion of the biological sample is then dispensed from the polymeric tube via the nozzle thereof onto one or more reagent pads. Finally, the cleaning solution is dispensed from the polymeric tube via the nozzle thereof into a cleaning well.

Figure 1:
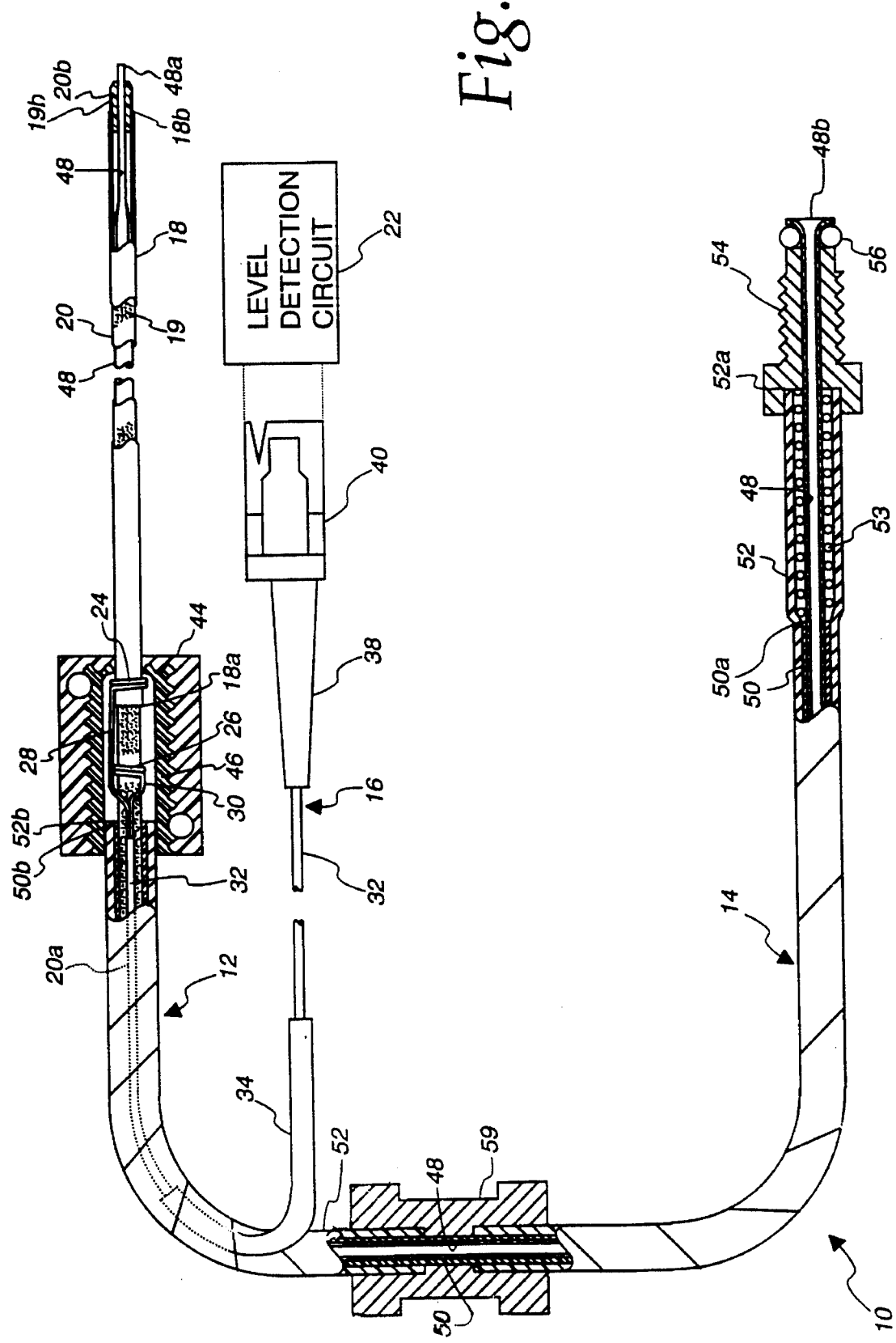
FIG. 1 is a plan view of the fluid sensing pipette embodying the present invention, with portions thereof broken away to show the internal structure.

While the invention is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all-modifications, equivalents, and alternatives falling within the spirit and scope of the invention as defined by the appended claims.

DETAILED DESCRIPTION OF THE PREFERRED EMBODIMENT

Turning now to the drawings, FIG. 1 illustrates a fluid sensing pipette 10 including a distal pipette section 12, a proximal pipette section 14, and a twisted wire section 16. The distal pipette section 12 includes an outer conductive tube 18 and an inner conductive tube 20 concentrically disposed within the outer conductive tube 18. The outer tube 18 extends along the distal pipette section 12 from a proximal location 18a to a distal location 18b. Similarly, the inner tube 20 extends from a proximal location 20a to a distal location 20b. The outer tube 18 is preferably composed of electro-polished stainless steel, and the inner tube is composed of stainless steel.

The outer tube 18 is insulated from the inner tube 20 by a uniform, consistent, and conformal polymeric coating 19 applied to the outer surface of the inner tube 20. In the preferred embodiment, the polymeric coating 19 is composed of a member of the Parylene polymer series (e.g., Parylene N, C, or D) manufactured by Union Carbide Corporation. The basic member of the series, Parylene N, is poly (paraxylylene). Parylene C is poly (2-chloro-para-xylylene), and Parylene D is poly (2,5-dichloro-para-xylylene). These three polymers have the following chemical structures:

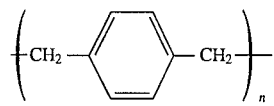

Parylene N

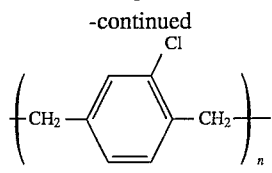

Parylene C

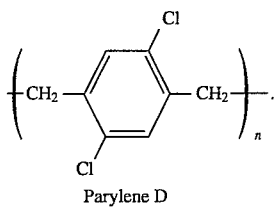

Parylene D

The selected Parylene polymer is vacuum deposited over substantially all of the outer surface of the inner tube 20 to form a conformal, thin, continuous, uniform adherent coating having a thickness of about 0.001'. The Parylene coating 19 extends from the proximal end 20a of the inner conductive tube 20 to a distal location 19b spaced a relatively short longitudinal distance away from the distal end 20b of the inner conductive tube 20. The Parylene coating 19 does not extend entirely to the distal end 20b so that a portion of the inner tube 20 remains exposed for impedance measurements when the pipette 10 is immersed in a liquid.

In addition to electrically insulating the outer conductive tube 18 from the inner conductive tube 20, the Parylene coating 19 prevents cross-contamination between different pipetted fluids, which may include biological samples, controls solutions, calibration solutions, and high protein solutions. Cross-contamination can results from the carryover of physical drops or constituents (e.g., proteins) of one pipetted fluid to another pipetted fluid. It is important for the Parylene coating 19 to prevent cross-contamination because the Parylene coating 19 is exposed in the region between the distal end 18b of the outer robe 18 and the distal end 19b of the Parylene coating 19. Since the Parylene coating 19 is hydrophobic, it prevents aqueous drops of pipetted fluids from adhering to the outer surface of the inner conductive tube 20 between the distal end 18b of the outer robe 18 and the distal end 19b of the Parylene coating 19. Moreover, although it is common for constituents of pipetted fluids to preferentially bind to certain types of hydrophobic plastics (See, e.g., Current Protocols in Immunology, Unit 7.28, Supplement 11, 1994), it has surprisingly been found that the Parylene coating 19 prevents constituents (e.g., proteins) of pipetted fluids from preferentially binding thereto. Thus, the Parylene coating 19 prevents cross-contamination between pipetted fluids resulting from carryover of either physical drops or constituents.

The conductive robes 18, 20 each serve as one electrode of a level detection circuit 22 connected to the proximal end of the twisted pair section 16. The conductive robes 18, 20 are coupled to the level detection circuit 22 by means of respective uninsulated wire connectors 24, 26 and respective insulated wires 28, 30. The wire connectors 24, 26 are preferably composed of fairly rigid, nickel-plated copper wire. One end of the wire connector 24 is wound about and soldered to the outer conductive tube 18, while the other end is connected to the insulated wire 28. Similarly, one end of the wire connector 26 is wound about and soldered to the inner conductive robe 20, while the other end is connected to the insulated wire 30. To maintain the integrity of the connections between the robes 18, 20 and the respective connectors 24, 26 and between the connectors 24, 26 and the respective wires 28, 30, an ABS machined housing 44 contains an epoxy potting compound 46 for protecting these connections. The housing 44 is also used to mount the pipette 10 onto an automated analyzer.

The wires 28, 30 form a conventional twisted wire pair extending through a plastic jacket 32 to a wire termination connector 40. The wires 28, 30 are connected to the termination connector 40 by means of crimping. At the Y-junction where the twisted wire section 16 splits off from the distal pipette section 12, the jacket 32 is reinforced with a plastic sleeve 34 shrink-wrapped about the jacket 32. Similarly, another plastic sleeve 38 is shrink-wrapped about the jacket 32 at a location adjacent the termination connector 40. The shrink-wrapped plastic sleeves 34, 38 prevent damage from being incurred to the twisted pair of wires 28, 30 at those locations where the wires are more susceptible to damage. The termination connector 40 is designed such that the wires 28, 30 must be separated from one another when crimped thereto. Therefore, it can be seen in FIG. 1 that the cross-sectional area of the sleeve 38 increases in the direction of the termination connector 40. The wire termination connector 40 is employed to connect the pipette 10 to the level detection circuit 22.

The pipette 10 is provided with a polymeric inner robe 48, preferably composed of TEFLON, for containing fluids which pass through the pipette 10. TEFLON is a trademark for tetrafluoroethylene polymers such as PFA and is available from E. I. Du Pont de Nemours Co. of Wilmington, Del. Between the proximal and distal locations 20a, 20b of the inner conductive robe 20, the polymeric tube 48 is concentrically disposed within the inner conductive tube 20. Furthermore, the polymeric robe 48 extends entirely through the distal and proximal pipette sections 12, 14, forming a nozzle 48a at one end and a flared portion 48b at the other end.

The polymeric robe 48 minimizes cross-contamination between different pipetted fluids, which may include biological samples, controls solutions, calibration solutions, and high protein solutions. As stated previously, cross-contamination may be caused by carryover of physical drops or constituents (e.g., proteins) of one pipetted fluid to another pipetted fluid. Carryover of physical drops occurs when physical drops strongly adhere to the pipette. Since the polymeric robe 48 is hydrophobic, aqueous samples are repelled from the inner surface of the tube 48. Therefore, after the pipette 10 operates on a fluid and the pipette 10 is cleansed with cleaning solution, no physical drops of that pipetted fluid remain adhered to the inner surface of the tube 48. Carryover of constituents such as proteins occurs when the proteins preferentially bind to the pipette. The TEFLON material of the polymeric tube 48 is resistant to such preferential binding.

To support the polymeric tube 48 and prevent the polymeric tube 48 from kinking, the tube 48 is threaded through a KYNAR sleeve 50, where KYNAR is the trademark of the Pennsalt Co. for the generic material polyvinylidene fluoride. The KYNAR sleeve 50 extends from a proximal location 50a to a distal location 50b within the housing 44. To further support and protect the polymeric tube 48, a spiral wrap 52 is disposed about the KYNAR sleeve 50. The spiral wrap 52 extends from a proximal location 52a within a pipette connector 54 to a distal location 52b within the housing 44. Within the distal pipette section 12, the jacket 32 containing the wires 28, 30 is disposed between the KYNAR sleeve 50 and the spiral wrap 52. The reinforcing sleeve 34 prevents damage to the jacket 32 or the wires 28, 30 at the point where the jacket 32 is separated from the spiral wrap 52.

To further prevent kinking of the polymeric tube 48 in a proximal portion of the proximal pipette section 14, an anti-kink spring 53 is disposed concentrically about the tube 48 and within the spiral wrap 52. The spring 53 is longitudinally positioned between the proximal end 50a of the KYNAR sleeve 50 and the pipette connector 54. The pipette 10 is further provided with a locator block 59, rigidly mounted within the automated analyzer, to prevent movement of the proximal pipette section 14 while the automated analyzer maneuvers the distal pipette section 12.

Figure 2:
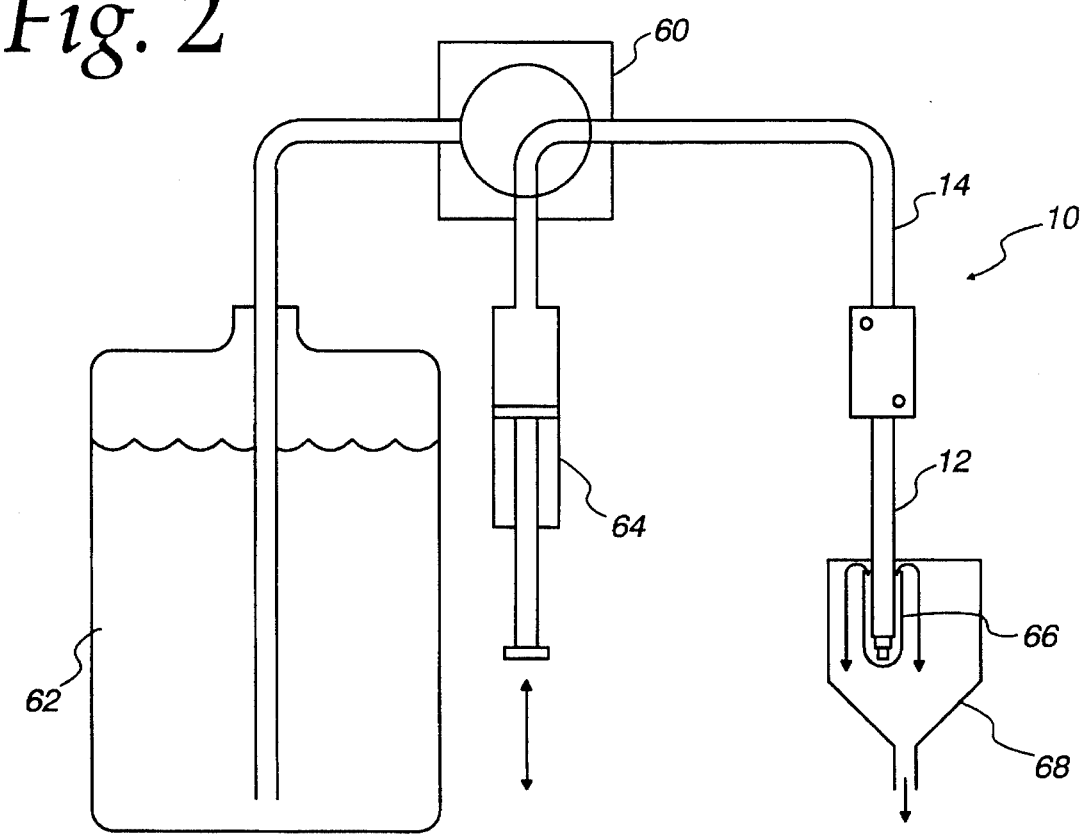
FIG. 2 illustrates a process for cleaning the fluid sensing pipette in FIG. 1.

The pipette connector 54 is engaged with a mating connector (not shown) which, in turn, is connected to a two-way, three-port valve 60 (FIG. 2). The valve 60 is then coupled to both a source of cleaning solution 62 and a syringe pump 64 (FIG. 2). The flared portion 48b of the polymeric robe 48 extends about a rubber O-ring 56 positioned between the pipette connector 54 and the mating connector. The rubber O-ring 56 cooperates with the flared portion 48b to prevent fluid leakage as cleaning solution passes from the source of cleaning solution and into the pipette 10.

Referring now to FIG. 2, prior to aspirating a biological sample into the pipette 10, the two-way valve 60 is switched to permit cleaning solution 62 to be pumped by the syringe pump 64 into the pipette 10 via the connector 54. The polymeric tube 48 of the pipette 10 is filled with the cleaning solution up to the nozzle 48a of the polymeric tube 48. Filling the polymeric tube 48 with the cleaning solution makes the polymeric tube 48 incompressible during subsequent aspiration of a biological sample. In other words, the cleaning solution prevents the polymeric tube 48 from collapsing in response to aspiration of a biological sample into the polymeric tube 48. In addition, falling the polymeric tube 48 with the cleaning solution allows the pipette 10 to subsequently aspirate a biological sample with accuracy and to accurately dispense small volumes of the biological sample onto multiple reagent pads.

After pumping the cleaning solution into the pipette 10, the two-way valve 60 is switched to permit the syringe pump 64 to aspirate a small volume (e.g., approximately 15 microliters) of air into the polymeric tube 48. After aspirating the small volume of air into the polymeric tube 48, the pipette 10 is immersed into a biological sample and the syringe pump 64 aspirates a relatively large volume (e.g., approximately 700 microliters) of the biological sample into the polymeric tube 48 of the pipette 10. As the biological sample is aspirated into the pipette 10, the previously aspirated volume of air and the cleaning solution are forced proximally through the polymeric tube 48. The small volume of air creates a small air gap between the aspirated biological sample and the cleaning solution to minimize mixing of the biological sample and the cleaning solution. The smooth inner surface of the polymeric tube 48 prevents any breakdown of this air gap. Once the entire volume of the biological sample is aspirated into the pipette 10, the biological sample fills the polymeric tube 48 from the nozzle 48a to approximately the location of the proximal end 50a of the KYNAR sleeve 50. The air gap separates the biological sample at this proximal location from the cleaning solution.

After aspirating the biological sample into the pipette 10, the biological sample is dispensed onto multiple reagent pads. While dispensing the biological sample onto the reagent pads, the air gap is maintained in the polymeric tube 48 between the biological sample and the cleaning solution. This air gap moves distally through the polymeric tube 48 as the biological sample is dispensed therefrom. Any leftover biological sample is dispensed into a discharge basin 68, which directs the dispensed leftover sample to a waste tank (not shown).

The pipette 10 is cleansed by switching the two-way valve 60 so as to permit additional cleaning solution 62 to be pumped by the syringe pump 64 into the pipette 10 via the connector 54. The cleaning solution is passed through the plastic tube 48 and expelled from the nozzle 48a thereof into a cylindrical well 66 within the discharge basin 68. The well 66 is constructed so that after the expelled cleaning solution strikes the bottom of the well 66, the expelled cleaning solution is forced back up around the outer surface of the pipette 10 between the inner surface of the well 66 and this outer surface of the pipette 10. The expelled cleaning solution then overflows out the top of the well 66 and is directed by the discharge basin 68 to the waste tank.

The distal outer surface of the pipette 10 is cleansed by the action of the cleaning solution being forced back up around the outer surface of the pipette 10 between the inner surface of the well 66 and the outer surface of the pipette 10. The well 66 is sufficiently deep to cleanse the outer surface of the nozzle 48a and the distal outer surfaces of the inner conductive tube 20 and outer conductive tube 18. In each sampling cycle, the amount of time required to cleanse the outer surface of the pipette 10 is dependent upon the surface area of that outer surface which must be cleansed. The larger the surface area of the outer surface, the longer the time required to cleanse that outer surface. Since it is advantageous to minimize the required time for cleansing the outer surface if the pipette 10, it is preferable to minimize the surface area of the outer surface by minimizing the outer diameter of the pipette 10.

In the pipette 10, the outer diameter of the pipette 10 is minimized by employing the thin, uniform, and consistent Parylene coating 19 over the inner conductive tube 20, as opposed to employing a separate and much thicker plastic sleeve between the outer and inner conductive tubes 18, 20. In the preferred embodiment, the outer conductive tube 18 has an outer diameter of approximately 0.083 inches and an inner diameter of approximately 0.077 inches; the inner conductive tube 20 has an outer diameter of approximately 0.072 inches and an inner diameter of approximately 0.064 inches; and the Parylene coating 19 over the inner conductive tube 20 has a thickness of approximately 0.001 inches. In addition, prior to being threaded through the inner conductive tube 20, the polymeric tube 48 has an outer diameter of approximately 0.070 inches and an inner diameter of 0.050 inches. To thread the polymeric tube 48 through the inner conductive tube 20, the polymeric tube 48 is first stretched to temporarily provide the tube 48 with a smaller outer diameter and permit the tube 48 to be inserted into the inner conductive tube 20. Due to memory retention, the polymeric tube 48 expands within the inner conductive tube 20 to firmly secure the polymeric tube 48 within the inner conductive tube 20.

Figure 4:
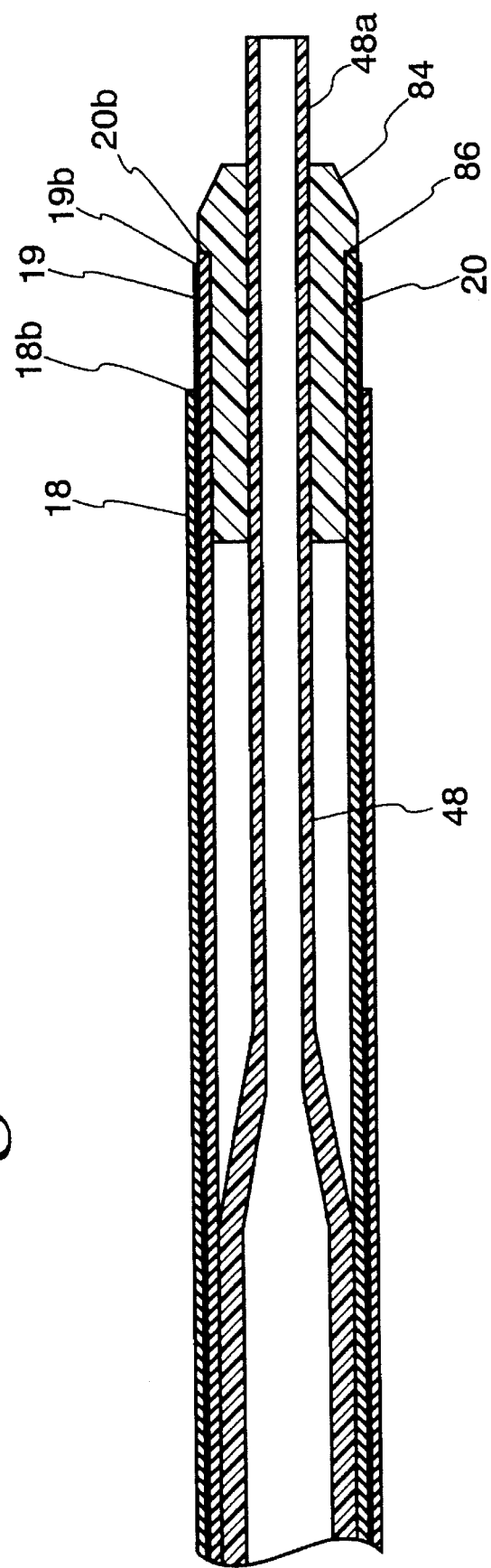
FIG. 4 is an enlarged plan view of a distal portion of the fluid sensing pipette in FIG. 1.

To prevent fluid from entering the region between the outer and inner tubes 18, 20 at the distal end 18b of the outer tube 18, the outer tube 18 is bonded over the inner tube 20 by a water resistant and electrically insulating epoxy. Moreover, as best shown in FIG. 4, a hydrophobic polymeric plug 84 with a generally cylindrical shape is inserted between the polymeric tube 48 and the inner conductive tube 20 at the distal end of the pipette 10. The plug 84, preferably composed of TEFLON, forms a shoulder 86 which abuts the distal end 20b of the inner conductive tube 20. The shoulder 86 facilitates accurate positioning of the plug 84 relative to the polymeric tube 48 and the inner conductive tube 20.

The plug 84 serves three primary functions. First, the plug 84 maintains the nozzle 48a of the polymeric tube 48 concentric with the inner conductive tube 20. Aligning the nozzle 48a concentrically with the inner tube 20 is important because the samples dispensed from the pipette 10 onto reagent pads must be centered within ±0.005 inches. Second, the plug 84 forms an impenetrable seal between the polymeric tube 48 and the inner conductive tube 20, thereby preventing fluid from entering the region between these two elements.

Third, the plug 84 prevents the polymeric tube 48 from dilating and eventually pulling back into the inner conductive tube 20 during a manufacturing process known as temperature cycling. The temperature cycling process involves repeatedly (1) heating the pipette 10 for a few minutes in an approximate 75° C. environment (e.g., an oven) and (2) cooling the pipette 10 for a few minutes in an approximate −40° C. environment (e.g, dry ice container). The foregoing steps of heating and cooling the pipette 10 are preferably repeated several times. As described above, during assembly of the pipette 10 the polymeric tube 48 is stretched and then inserted within the inner conductive tube 20. Following insertion of the polymeric tube 48 within the inner conductive tube 20, the polymeric tube 48 tends to pull back into the inner conductive tube 20 because of the inherent memory of the polymeric material. To relieve any memory retained by the nozzle 48a of the polymeric tube 48 following insertion of the polymeric tube 48 into the inner tube 20, the pipette 10 is subjected to the temperature cycling process described above. Prior to undergoing the temperature cycling process, the plug 84 is inserted between the inner conductive tube 20 and the polymeric tube 48. This plug 84 resists the tendency of the polymeric tube 48 and its nozzle 48a to pull back into the inner conductive tube 20 during the temperature cycling process. By relieving (erasing) the memory of the polymeric tube 48, the temperature cycling process stabilizes the length of the nozzle 48a. In the preferred embodiment, the pipette 10 is provided with an extra long nozzle prior to subjecting the pipette 10 to the temperature cycling process. Once the temperature cycling process stabilizes the entire length of this extra long nozzle, the extra long nozzle is cut down in size to form the nozzle 48a.

An important feature of the present invention is that the pipette 10 is designed to detect entry of the distal tip of the pipette 10 into a sample within a test tube. This fluid sensing feature is accomplished by the outer and inner conductive tubes 18, 20, in conjunction with the level detection circuit 22. The outer conductive tube 18 forms a first electrode which is coupled to the level detection circuit 22 using the wire connector 24 and the wire 28. The inner conductive tube 20 forms a second electrode which is coupled to the level detection circuit 22 using the wire connector 26 and the wire 30. In response to outer and inner conductive tubes 18, 20 contacting a conductive fluid sample, the level detection circuit 22 senses a decrease in impedance between the first and second electrodes. If the impedance between the electrodes falls below a predetermined threshold, then the circuit 22 detects entry of the pipette tip into the sample.

In an automated analyzer, this detection by the circuit 22 is used to signal a motor to stop the downward motion of the pipette 10 into the sample. The pipette 10 then aspirates a certain desired volume of sample and automatically dispenses the aspirated volume over multiple reagent pads. After dispensing the aspirated sample, the pipette tip enters the well 66 (FIG. 2) where it is thoroughly cleansed of the sample in the manner previously described.

Figure 3:
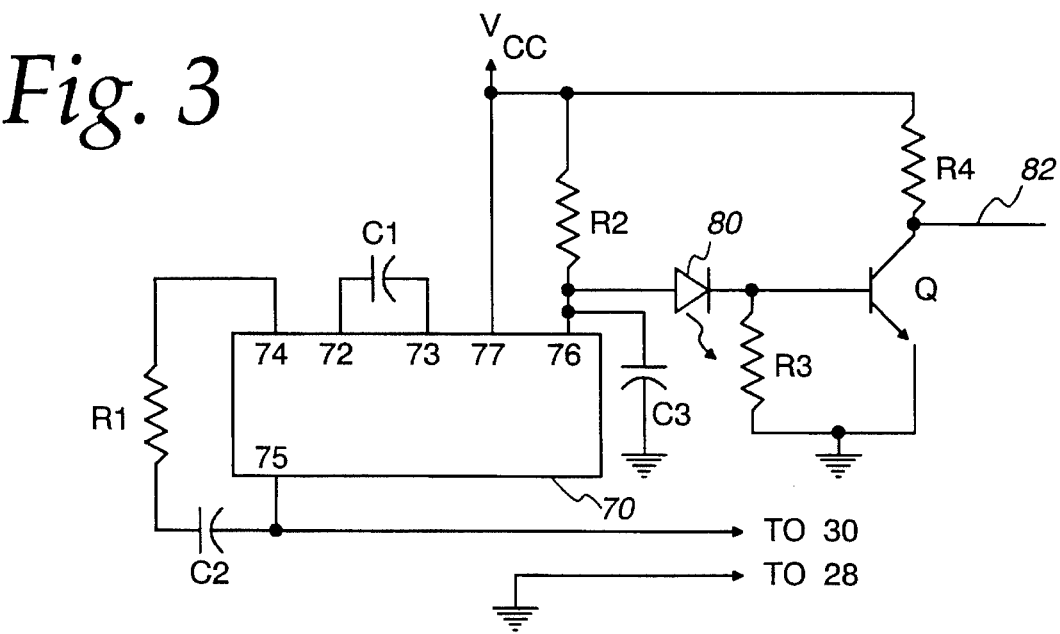
FIG. 3 is a schematic diagram the level detection circuit employed by the fluid sensing pipette in FIG. 1.

FIG. 3 is a schematic diagram of the level detection circuit 22, which is connected to the pipette 10 using the termination connector 40. The illustrated circuit 22 employs an LM1830N fluid detector 70 manufactured by National Semiconductor Corporation. The fluid detector 70 is a monolithic bipolar integrated circuit designed for use in fluid detection systems. The integrated circuit 70 internally contains both an oscillator and voltage detector, and the circuit 70 includes a plurality of terminals 72–77. To complete the internal oscillator circuit, an external capacitor C1 is connected between the terminals 72 and 73 of the integrated circuit 70. This produces an oscillating output signal at the terminal 74 of the integrated circuit 70. The frequency of oscillation of the oscillating output signal is inversely proportional to the value of the external capacitor C1. In the preferred embodiment, the capacitor C1 has a value 0.001 microfarads so that the output frequency is approximately 8 kilohertz.

The oscillating output signal at the terminal 74 of the integrated circuit 70 is coupled through a resistor R1 and a ceramic capacitor C2 to the voltage detector input at the terminal 75 of the integrated circuit 70. In the preferred embodiment, the resistor R1 has a value of 20 kiloohms, and the capacitor C2 has a value of 0.1 microfarads. These values cause the level detector circuit 22 to have an impedance threshold of approximately 16 kiloohms, below which the circuit 22 detects fluid and above which the circuit 22 does not detect fluid. The detector input terminal 75 is also connected to the wire 30 which, in turn, is connected to the inner conductive tube 20 of the pipette 10. The outer conductive tube 18 is grounded by connecting the wire 28 to ground.

Power is supplied to the integrated circuit 70 by connecting a +12 volt DC source ("Vcc") to the power supply terminal 77, and a terminal 78 of the integrated circuit 70 is connected to ground. The output terminal 76 is coupled through a 1.2 kiloohm resistor R2 to the voltage source Vcc. Also, the output terminal 76 is coupled through a light-emitting diode (LED) 80 to the base of a transistor Q, which preferably is a 2N4124 transistor manufactured by National Semiconductor Corporation. The transistor emitter is connected to ground, and the transistor base is coupled through a 100 ohm resistor R3 to ground. The transistor collector is coupled through a 3.3 kiloohm resistor R4 to the power source Vcc. A filter capacitor C3, preferably having a value of 15 microfarads, is connected between the terminal 76 and ground. The time constant determined by the resistor R2 and the capacitor C3 determine the response time of the level detection circuit 22. The LED 80 and the transistor Q do not conduct until the output terminal 76 ceases to conduct and the capacitor C3 charges through the resistor R2.

The level detection circuit 22 determines the presence or absence of fluid by comparing the impedance between the outer and inner conductive tubes 18, 20 with the preset threshold impedance of 16 kiloohms. In response to the pipette 10 being located outside of a fluid, the oscillator output signal from the terminal 74 is coupled to the detector input terminal 75 so as to turn on an internal transistor located within the integrated circuit 70 and coupled to the output terminal 76. As a result, most of the current passing through the resistor R2 is diverted into the output terminal 76 of the integrated circuit 70. Since an insufficient amount of current passes through the LED 80, the LED 80 is "Off", the transistor Q is nonconducting, and the transistor output along a line 82 is logic HI.

In response to the pipette being located within a conductive fluid (i.e., ionic fluid) and the impedance between the outer and inner conductive tubes 18, 20 falling below the threshold of 16 kiloohms, the output terminal 76 of the integrated circuit is nonconducting. Thus, a sufficient amount of current passes through the LED 80 to turn "On" the LED 80. With the LED 80 "On", the transistor Q is conducting and the transistor output along the line 82 is logic LOW.

Fluids with low ionic content have a higher impedance than fluids with a higher ionic content. Since the threshold impedance of the level detection circuit 22 is 16 kiloohms, the pipette 10 is sensitive to a variety of higher ionic fluids (e.g., urine samples) and is nonresponsive to lower ionic fluids and de-ionized fluids. The level detection circuit 22 allows the depth of immersion of the pipette 10 into a higher ionic fluid sample to be carefully controlled such that the pipette 10 is submerged into the sample just deep enough to aspirate the sample without drawing up any air. This controlled depth of immersion causes the sample to contact only a very small fraction of the pipette 10, thereby minimizing the mount of the pipette 10 which must be cleansed in each sampling cycle. By minimizing the amount of the pipette 10 which must be cleansed, the amount of time required to cleanse the pipette 10 is minimized. The cleaning solution used to cleanse the pipette 10 has a sufficiently low ionic content that the level detection circuit 22 does not mistake the cleaning solution for the sample.

What is claimed is:

1. A fluid sensing pipette, comprising:

an outer conductive tube forming a first electrode;

an inner conductive tube forming a second electrode, said inner conductive tube disposed concentrically within said outer conductive tube, an outer surface of said inner conductive tube coated with a thin, uniform, and consistent polymer coating to insulate said inner conductive tube from said outer conductive tube;

a hydrophobic polymeric tube disposed concentrically within said inner conductive tube; and a level detection circuit, coupled to said inner and outer conductive tubes, for determining an impedance between said first and second electrodes and for generating a control signal in response to the impedance falling below a predetermined threshold wherein said polymer coating is selected from the group consisting of poly (para-xylylene), poly (2-chloro-para-xylylene), and poly (2,5-dichloro-para-xylylnene.

2. The fluid sensing pipette of claim 1, wherein said polymer coating has a thickness of approximately 0.001 inches.

3. The fluid sensing pipette of claim 1, wherein said polymeric tube extends beyond a distal end of said inner conductive tube to form a nozzle.

4. The fluid sensing pipette of claim 3, wherein said inner conductive tube extends beyond a distal end of said outer conductive tube.

5. The fluid sensing pipette of claim 4, wherein a distal portion of said outer surface of said inner conductive tube is free of said polymeric coating, and wherein said polymeric coating extends beyond said distal end of said outer conductive tube.

6. A fluid sensing pipette, comprising:

an outer conductive tube forming a first electrode;

an inner conductive tube forming a second electrode, said inner conductive tube disposed concentrically within said outer conductive tube, an outer surface of said inner conductive tube coated with a thin, uniform, and consistent polymer coating to insulate said inner conductive tube from said outer conductive tube;

a hydrophobic polymeric tube disposed concentrically within said inner conductive tube;

a hydrophobic polymeric plug disposed between said inner conductive tube and said polymeric tube in close proximity to a distal end of said polymeric tube so as to prevent fluid from entering between said inner conductive tube and said polymeric tube; and a level detection circuit, coupled to said inner and outer conductive tubes, for determining an impedance between said first and second electrodes and for generating a control signal in response to the impedance falling below a predetermined threshold wherein said polymer coating is selected from the group consisting of poly (para-xylylene), poly (2-chloro-para-xylylene), and poly (2,5-dichloro-para-xylylene.

7. A method of manufacturing a fluid sensing pipette, comprising the steps of:

providing an outer conductive tube forming a first electrode;

providing an inner conductive tube forming a second electrode;

coating an outer surface of said inner conductive tube with a thin, uniform, and consistent polymer coating;

positioning said inner conductive tube concentrically within said outer conductive tube, said polymer coating insulating said inner conductive tube from said outer conductive tube;

inserting a hydrophobic polymeric tube concentrically within said inner conductive tube, said polymeric tube forming a nozzle protruding from one end of said inner conductive tube;

repeatedly heating and cooling said outer conductive tube, said inner conductive tube, said polymer coating, and said polymeric tube to stabilize the length of said nozzle of said polymeric tube; and coupling said inner and outer conductive tubes to a level detection circuit for determining an impedance between said first and second electrodes and for generating a control signal in response to the impedance falling below a predetermined threshold wherein said polymer coating is selected from the group consisting of poly (para-xylylene), poly (2-chloro-para-xylylene), and poly (2,5-dichloro-para-xylylene.

8. The method of claim 7, wherein said step of repeatedly heating and cooling said outer conductive tube, said inner conductive tube, said polymer coating, and said polymeric tube includes (a) heating at approximately 75° C. for a few minutes, (b) cooling at approximately −40° C. for a few minutes, and (c) repeating steps (a) and (b) a predetermined number of times.

9. The method of claim 7, further including the step of inserting a hydrophobic polymeric plug between said inner conductive tube and said polymeric tube adjacent said nozzle of said polymeric tube so as to prevent fluid from entering between said inner conductive tube and said polymeric tube.

10. A method of using a fluid sensing pipette including (a) an outer conductive tube forming a first electrode, (b) an inner conductive tube forming a second electrode, said inner conductive tube disposed concentrically within said outer conductive tube, an outer surface of said inner conductive tube coated with a thin, uniform, and consistent polymer coating to insulate said inner conductive tube from said outer conductive tube, (c) a hydrophobic polymeric tube disposed concentrically within said inner conductive tube, said polymeric tube having a distal end and a proximal end, and (d) a level detection circuit, coupled to said inner and outer conductive tubes, for determining an impedance between said first and second electrodes and for generating a control signal in response to the impedance falling below a predetermined threshold, said method comprising the steps of:

pumping cleaning solution into said polymeric tube via the proximal end thereof;

aspirating air into said polymeric tube via the distal end thereof;

aspirating a biological sample into said polymeric tube via the distal end thereof, the aspirated air creating an air gap between the cleaning solution and the aspirated biological sample;

dispensing at least a portion of the biological sample from the polymeric tube via the distal end thereof onto one or more reagent pads; and dispensing the cleaning solution from the polymeric tube via the distal end thereof into a cleaning well, wherein said polymer coating is selected from the group consisting of poly(para-xylylene), poly (2-chloro-para-yxlylene), and poly (2,5-dichloro-para-xylylene.

* * * * *